US011645791B2

(12) United States Patent
Huang et al.

(10) Patent No.: US 11,645,791 B2
(45) Date of Patent: May 9, 2023

(54) SYSTEMS AND METHODS FOR JOINT RECONSTRUCTION AND SEGMENTATION OF ORGANS FROM MAGNETIC RESONANCE IMAGING DATA

(71) Applicant: Rutgers, The State University of New Jersey, New Brunswick, NJ (US)

(72) Inventors: Qiaoying Huang, Edison, NJ (US); Dimitris Metaxas, Princeton, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 57 days.

(21) Appl. No.: 17/072,632

(22) Filed: Oct. 16, 2020

(65) Prior Publication Data

US 2021/0118205 A1 Apr. 22, 2021

Related U.S. Application Data

(60) Provisional application No. 62/916,455, filed on Oct. 17, 2019.

(51) Int. Cl.
*G06K 9/00* (2022.01)
*G06T 11/00* (2006.01)
(Continued)

(52) U.S. Cl.
CPC ............. *G06T 11/006* (2013.01); *G06T 7/11* (2017.01); *G06T 7/13* (2017.01); *G06T 7/20* (2013.01);
(Continued)

(58) Field of Classification Search
CPC .......................................... G06T 2207/10088
See application file for complete search history.

(56) References Cited

U.S. PATENT DOCUMENTS 9,589,374 B1 * 3/2017 Gao ..................... A61B 6/5211
2008/0234578 A1 * 9/2008 Claus ................... A61B 8/4416
600/437
(Continued)

OTHER PUBLICATIONS

C. Qin, J. Schlemper, J. Caballero, A. N. Price, J. V. Hajnal and D. Rueckert, "Convolutional Recurrent Neural Networks for Dynamic MR Image Reconstruction," in IEEE Transactions on Medical Imaging, vol. 38, No. 1, pp. 280-290, Jan. 2019, doi: 10.1109/TMI.2018.2863670. (Year: 2019).*

(Continued)

*Primary Examiner* — Hadi Akhavannik
(74) *Attorney, Agent, or Firm* — McCarter & English, LLP

(57) ABSTRACT

Systems and methods for joint reconstruction and segmentation of organs from magnetic resonance imaging (MRI) data are provided. Sparse MRI data is received at a computer system, which jointly processes the MRI data using a plurality of reconstruction and segmentation processes. The MRI data is processed using a joint reconstruction and segmentation process to identify an organ from the MRI data. Additionally, the MRI data is processed using a channel-wise attention network to perform static reconstruction of the organ from the MRI data. Further, the MRI data is processed using a motion-guided network to perform dynamic reconstruction of the organ from the MRI data. The joint processing allows for rapid static and dynamic reconstruction and segmentation of organs from sparse MRI data, with particular advantage in clinical settings.

27 Claims, 13 Drawing Sheets

(51) Int. Cl.
*G06T 7/11* (2017.01)
*G06T 7/13* (2017.01)
*G06T 7/20* (2017.01)

(52) U.S. Cl.
CPC .............. *G06T 2207/10088* (2013.01); *G06T 2207/20084* (2013.01); *G06T 2207/30048* (2013.01); *G06T 2211/412* (2013.01)

(56) References Cited

U.S. PATENT DOCUMENTS

| | | | | |
|---|---|---|---|---|
| 2010/0194389 | A1* | 8/2010 | Sutton | G01R 33/4818 324/309 |
| 2014/0167753 | A1* | 6/2014 | Sperl | G01R 33/56341 324/309 |
| 2017/0053402 | A1* | 2/2017 | Migukin | G06T 7/0012 |
| 2018/0075581 | A1* | 3/2018 | Shi | G06T 3/4046 |
| 2018/0325477 | A1* | 11/2018 | Wang | A61B 5/055 |
| 2019/0172230 | A1 | 6/2019 | Mailhe et al. | |
| 2019/0213779 | A1* | 7/2019 | Sutton | G06T 19/00 |
| 2020/0065969 | A1* | 2/2020 | Huang | G06T 7/0012 |

OTHER PUBLICATIONS

Huang, et al.," FR-Net: Joint Reconstruction and Segmentation in Compressed Sensing Cardiac MRI," Functional Imaging and Modeling of the Heart (2019) (9 pages).

Huang, et al., "MRI Reconstruction via Cascaded Channel-Wise Attention Network," 2019 IEEE 16th International Symposium on Biomedical Imaging (5 pages).

Huang, et al., "MODRN: Dynamic MRI Reconstrution with Motion-Guided Network," Proceedings of Machine Learning Research (2019) (11 pages).

Huang, et al., "Dynamic MRI Reconstruction with Motion-Guided Network," Proceedings of Machine Learning Research (2019) (10 pages).

* cited by examiner

SYSTEMS AND METHODS FOR JOINT RECONSTRUCTION AND SEGMENTATION OF ORGANS FROM MAGNETIC RESONANCE IMAGING DATA

RELATED APPLICATIONS

The present application claims the benefit of U.S. Provisional Application Ser. No. 62/916,455 filed on Oct. 17, 2019, the entire disclosure of which is expressly incorporated herein by reference.

BACKGROUND

Technical Field

The present disclosure relates generally to the field of medical imaging and computer vision technology. More specifically, the present invention relates to systems and methods for joint reconstruction and segmentation of organs from magnetic resonance imaging ("MRI") data.

Related Art

Magnetic resonance imaging ("MRI") is widely used due to its high resolution, high contrast, and no radiation, but a fully-sampled MRI scan requires a lot of time for a patient to undergo the scan. Such scans could greatly benefit from advances being made in machine learning techniques (artificial intelligence or "AI") for MRI reconstruction of undersampled MRI scan data that specifically benefit cardiac MRIs. In particular, there is a need to improve the performance of reconstruction (making current MRI scans faster), remove the need for manual intervention, and support reconstruction and organ segmentation where there is patient and/or organ movement, thereby improving the ability to reconstruct MRI images of the heart and other organs, as well as performing cardiac segmentation.

Better MRI imaging of the heart that requires less time and the ability to use AI techniques to address motion and organ segmentation is of particular importance. One of the biggest hurdles to more extensive use of cardiac MRI is how long the exam takes (over an hour) and how complicated the procedures are (patients need to hold their breath during certain sequences). The breath hold is necessary to cease any motion that might obscure the image, but not all patients are able to do this for the required length of time or repeatedly. There is also a need to reduce manual intervention/correction required by current approaches to myocardium segmentation in cardiac magnetic resonance (MR) images which play a vital role in clinical diagnosis of the cardiovascular diseases. Because of the low contrast and large variation in intensity and shapes, myocardium segmentation has been a challenging task. Finally, there is a need to reduce both scan and reconstruction time. Accordingly, the systems and methods of the present address the foregoing, and other, needs.

SUMMARY

The present disclosure relates to systems and methods for joint reconstruction and segmentation of organs from magnetic resonance imaging (MRI) data. Sparse MRI data (k-space MRI data) is received at a computer system. The computer system jointly processes the MRI data using a plurality of reconstruction and segmentation processes. For example, the MRI data is processed using a joint reconstruction and segmentation process to identify an organ from the MRI data. Additionally, the MRI data is processed using a channel-wise attention network to perform static reconstruction of the organ from the MRI data. Further, the MRI data can be processed using a motion-guided network to perform dynamic reconstruction of the organ from the MRI data. Advantageously, the joint processing performed by the systems and methods of the present disclosure allow for rapid static and dynamic reconstruction and segmentation of organs from sparse MRI data, with particular advantage in clinical settings.

BRIEF DESCRIPTION OF THE DRAWINGS

The foregoing features of the invention will be apparent from the following Detailed Description, taken in connection with the accompanying drawings, in which.

DETAILED DESCRIPTION

The present disclosure relates to systems and methods for joint reconstruction and segmentation of organs from MRI data, as discussed in detail below in connection with FIGS. 1-13.

Figure 1:
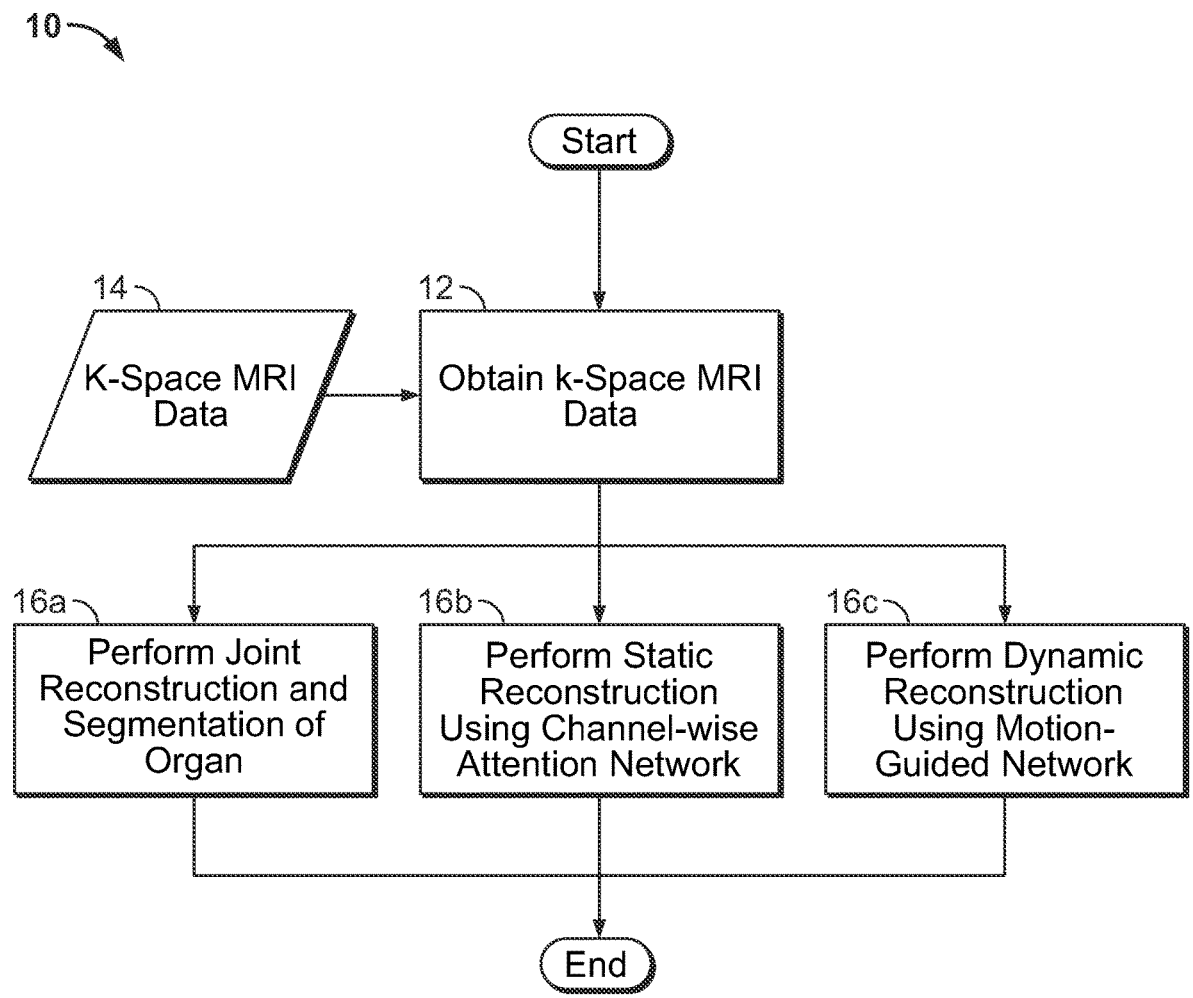
FIG. 1 is a flowchart illustrating overall processing steps carried out by the systems and methods of the present disclosure.

FIG. 1 is a flowchart illustrating overall processing steps carried out by the systems and methods of the present disclosure, indicated generally at 10. In step 12, the system obtains k-space MRI data 14 from a suitable source, such as directly from an MRI scanner, from a computer system, and/or from a database of MRI data. The k-space MRI data 14 typically is undersampled data generated by the MRI machine when a scan is performed on a patient. In the past, the k-space MRI data 14 often did not have sufficient information to allow for adequate reconstruction and segmentation of organs in clinical applications, including both static and dynamic reconstruction and segmentation. Importantly, the three joint processes 16a-16c of the systems and methods of the present disclosure, discussed in more detail below, are performed jointly (or, in series) on the k-space MRI data 14 to allow for joint reconstruction and segmentation of organs, including both static and dynamic reconstruction and segmentation. This represents a significant improvement in the speed of MRI scans as well as the ability to perform dynamic and static reconstruction and segmentation of organs using sparse k-space MRI data. The processes 16a-16c include process 16a for performing joint reconstruction and segmentation of the organ (such as the heart or other organ), process 16b for performing static reconstruction of the organ using a channel-wise attention network, and process 16c for performing dynamic reconstruction of the organ using a motion-guided network. Each of these processes will be described in greater detail below.

It is noted that one or more of the processes disclosed herein (e.g., the processing steps shown in FIG. 1 and more fully described herein with reference to the other figures) could be performed via a processor in communication with, or embedded within, an MRI scanner. Indeed, such processor could be an existing processor of an MRI scanner that is programmed in accordance with the processes disclosed herein. Further, the processes disclosed herein could be performed by a standalone processor that processes MRI image data, such as a personal computer, server, cloud computing device, smart phone, or any other suitable computing device. Further, the processes discussed herein could access MRI image data stored in a memory (e.g., a memory of an MRI scanner or a separate memory), and could be embodied as computer-readable instructions executed by a processor in communication with the memory which process the MRI image data as disclosed herein.

Additionally, it is noted that the processes 16a-16c need not occur jointly, and that each process can be operated independently and with varying input data without departing from the spirit or scope of the present invention. For example, if the input data is static data, process 16b (independent of processes 16a and 16c) can be utilized to process the static data in order to perform reconstruction of an organ using the channel-wise attention network disclosed herein. As another example, if the input data is dynamic data, process 16c (independent of processes 16a and 16b) can be utilized to perform dynamic reconstruction of the organ using the motion-guided network disclosed herein. Still further, any combination of the processes 16a-16c could be performed in any desire order. For example, the process 16a can be used to perform segmentation of the organ using the joint reconstruction and segmentation network disclosed herein, in combination with one, or both, of the processes 16b-16c.

Figure 2:
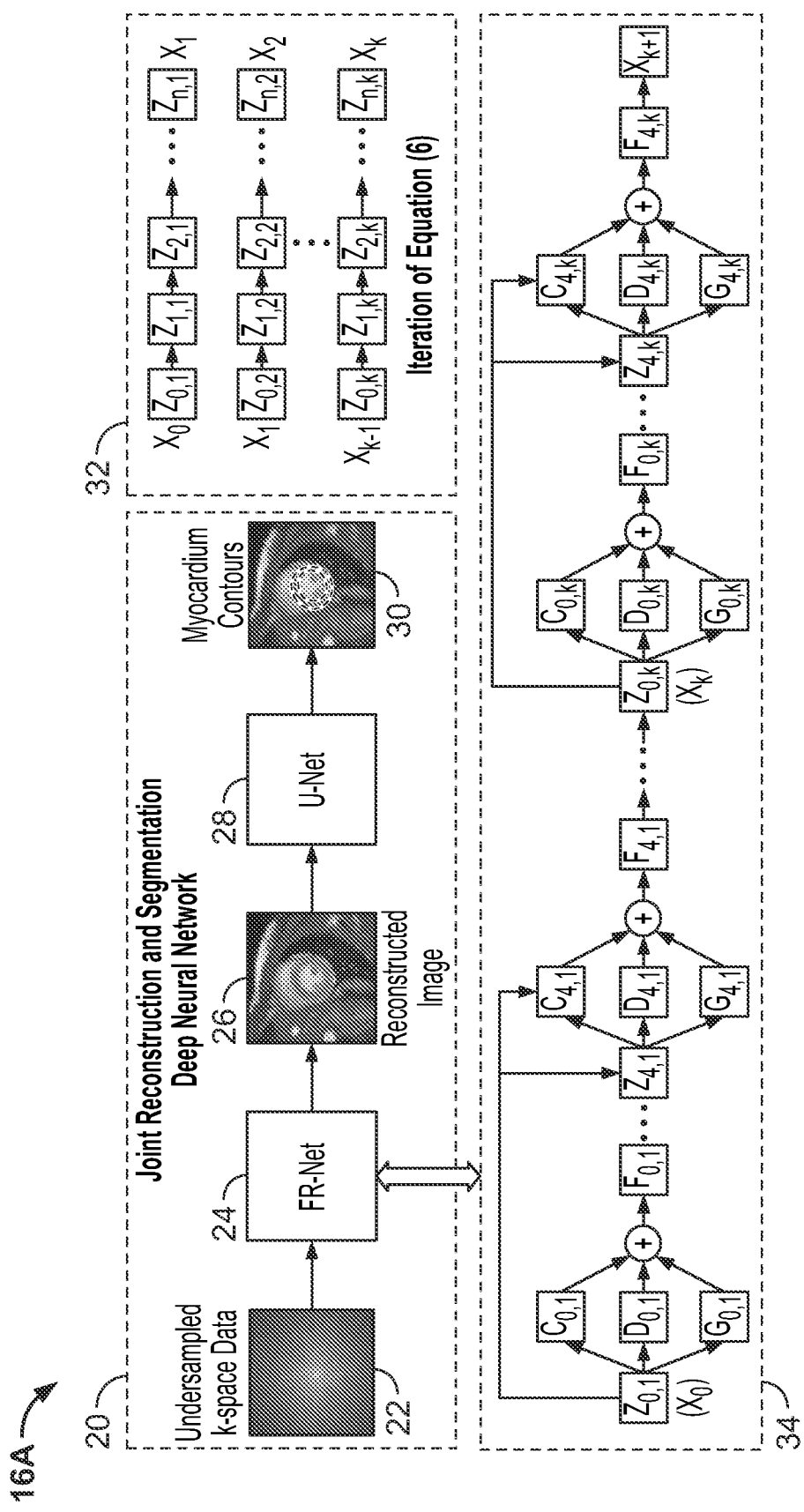
FIG. 2 is a diagram illustrating processing performed by processing step 16a of FIG. 1, in greater detail.

FIG. 2 is a diagram illustrating processing performed by process 16a of FIG. 1, in greater detail. As shown in FIG. 2, process 16a is a joint image reconstruction and myocardium segmentation deep neural network based approach that has the following structure: an image reconstruction network and a segmentation network.

The general objective of a CS-MRI reconstruction problem is to find the best reconstructed image x such that it minimizes the difference between undersampled data in k-space y, and undersampled data converted from x through the Fourier transform. The problem is formalized as follows:

$$x^* = \arg\min_x \frac{1}{2} \|E(F(x)) - y\|_2^2 + \lambda g(x), \quad (1)$$

where F is Fourier transform, E is an undersampled matrix and $\lambda g(\cdot)$ is a weighted regularization term. In MRI image reconstruction, the regularization function g usually takes $\ell_1$-norm or total variation norm.

Let $f(x) = \frac{1}{2}\|E(F(x)) - y\|_2^2$. Equation (1) immediately above is solvable if f is a smooth convex function with a Lipschitz continuous gradient L(f) and g is a continuous convex function and possibly nonsmooth. For any L>0, consider the following quadratic approximation of Equation (1) at a given point x.

$$Q_L(x, x') = f(x') + (x-x') \cdot \nabla f(x') + \frac{L}{2}\|x-x'\|^2 + \lambda g(x), \quad (2)$$

which admits a unique minimizer $p_L$. By ignoring constant terms related to x', we can rewrite $p_L$ as:

$$p_L(x') = \arg\min\{Q_L(x, x')\} = \arg\min_x\left\{\lambda g(x) + \frac{L}{2}\left\|x - \left(x' - \frac{1}{L}\nabla f(x')\right)\right\|^2\right\}, \quad (3)$$

According to Equation (3) immediately above and reconstruction problem Equation (1) immediately above, we can compute $x_k$ iteratively using the following minimization approach:

$$x_k = \arg\min_x\left\{\lambda g(x) + \frac{L_k}{2}\left\|x - \left(v_k - \frac{1}{L_k}\nabla f(v_k)\right)\right\|^2\right\}, \quad (4)$$

where $v_k$ is a linear combination of $x_{k-1}$ and $x_{k-2}$ from the previous two iterations and $L_k$ is a constant chosen by specific rule in the backtracking FISTA. This can generate a sequence of $\{x_1, x_2, \ldots, x_k\}$. In theory, if k goes to infinity, then $x_k$ can approximate the optimal solution of Equation (1) immediately above. In order to speed up the converge, $x_k$ is replaced by $v_k$, a linear combination of $x_{k-1}$ and $x_{k-2}$.

Note that in our MRI reconstruction problem, the gradient of $f(v_k)$ is defined as: $\nabla f(v_k) = F^T(E(F(v_k))-y)$, where $F^T$ represents inverse Fourier transform. For specific forms of $g(\cdot)$ such as $\ell_1$ norm, we can derive a closed form of $x_k$ and then obtain the solution of $x_k$ through gradient descent. More generally, we use gradient descent to generate a sequence of $\{z_{k,n}\}$ that gradually converges to $x_k$. Then we can generalize the problem to any form of $g(\cdot)$. Basically, $z_{k,n}$ is computed as follows:

$$z_{k,n} = z_{k,n-1} - \mu\{\lambda \nabla g(z_{k,n-1}) + L_k(z_{k,n-1} - v_k) + F^T(E(F(v_k)) - y)\}, \quad (5)$$

where μ denotes the gradient step and $\nabla g(\cdot)$ denotes the gradient of $g(\cdot)$. FIG. 2 shows the relationship between z and x. Suppose the input is $x_i$. Using Equation (5) immediately above iteratively n times, we can estimate $x_{i+1}$. Hence, there are n steps between $x_i$ and $x_{i+1}$. $z_{i,j}$ denotes the $j^{th}$ step between $x_i$ and $x_{i+1}$.

However, there are several drawbacks in this FISTA-based computational framework. First, it is very hard to derive a closed form of $x_k$ when $g(\cdot)$ is one of such joint norms. Second, it requires a huge amount of computation to find a good solution using the iterative process. Furthermore, it is time-consuming to find a good step size μ, since it varies given different undersampling rates. Additionally, $L_k$ is chosen according to rigorous conditions in backtracking FISTA, so it is sometimes hard to satisfy all conditions.

In order to overcome the aforementioned difficulties, we first propose a deep neural network model called FR-Net for MRI reconstruction. Specifically, we create a corresponding neural network for $x_k$ that can be solved via gradient descent. One advantage is that the neural network can be adapted to different forms of $g(\cdot)$ and hence closed form derivation is no longer required. Suppose at step k, the optimal value of Equation (4) immediately above is $x_k$. At each iteration n in the gradient descent, a value $z_{k-1,n}$ is generated to approximate $x_k$. As n becomes larger, $z_{k-1,n}$ converges to $x_k$. FIG. 2 shows how to iteratively compute z and x. Process 16a includes the use of a joint reconstruction and segmentation deep neural network 20 which processes undersampled k-space data 22, an FR-Net 24 which generates a reconstructed image 26, and a U-net (discussed below) 28 which generates an image 30 indicating myocardium contours. Process 16a also includes an iteration block 32 and processing chain 34, both discussed below.

In order to solve Equation (5) immediately above, we need to come out the close form of $\nabla g(z_{i,j})$. However, the regularization term g is always complicated. For example, it can be a joint norm whose gradient is hard to derive. Therefore, we replace g(•) with a convolution neural network $G_k$. The intuition is that the convolutional layer has powerful ability of feature representation that it can generalize to any regularization norms. Specifically, $G_k$ takes as input k-space data of a shape 256×256 and outputs feature vectors of the same shape. It consists of three convolution layers and each uses 3×3 kernels with 32 channels, followed by a Batch Normalization layer and a PReLU activation layer. The advantage of $G_k$ over g(•) is that convolution neural networks can be generalized to any form of regularization term and hence derivation of closed form of g(•) is no longer needed. The second modification is that we substitute $L_k$ with a fully connected layer called difference layer $D_k$ since $L_k$ is not easy to compute under some rigorous constraints in backtracking FISTA. Furthermore, $F^T(E(Fv_k)-y)$ is a constant value and we name it as $C_k$. The outputs of $G_k$, $D_k$ and $C_k$ are combined through element-wise addition and connected to another fully connected layer $F_k$. Finally, equation (5) is transformed to:

$$x_k = z_{n-1} - F_k\{(G_{k-1}(z_{n-1}) + D_k(z_{n-1} - v_k) + C_k(v_k)\} \quad (6)$$

Table 1, below, shows the average reconstruction performance of 3-fold cross validation performed by the process 16a:

between two originally-isolated models to become capable of learning parameters through backpropagation of shared gradients in the whole pipeline. From the perspective of model effectiveness and training efficiency, this mechanism allows two models to mutually benefit from each other. FR-Net 26 passes to the input of U-Net 28 the on-the-fly features of the "reconstructed image" instead of fixed noisy images so that features are shared and learned by both models. Meanwhile, U-Net 28 directly backpropagates gradients to FR-Net 24 to make the whole model more segmentation-oriented.

Technically speaking, let Re be the reconstruction network parameterized by θ and $S_\Phi$ be the segmentation network parameterized by Φ. In our application, $R_\theta$ and $S_\Phi$ respectively represent FR-Net 24 and U-Net 28. Let y denote the input of k-space data. The reconstructed image is $R_\theta(y)$ and the segmentation result is $S_\Phi(R_\theta(y))$. Note that the input of the segmentation network is the output of the reconstruction network and hence the parameters and θ are updated simultaneously.

We also define a combination loss $\ell_{com}$ which is based on both the reconstruction loss function $l_R$ and the segmentation loss function $l_S$. $\ell_{com}$ is defined as: $\pounds_{com} = l_R(R^\theta(y), \tilde{x}) + \beta \cdot l_S(S^\Phi(R^\theta(y)), \tilde{x})$, where $\tilde{x}$ is the ground truth of the reconstruction image and $\tilde{x}$ is the ground truth of the reconstruction mask. B is the hyper-parameter that balances between reconstruction and segmentation performances. Reconstruction loss $l_R$ is defined as $l_1$ loss and segmentation loss $l_s$ is defined as dice loss. During the training procedure, the key issue is to find an optimal equilibrium between reconstruction and segmentation such that they are mutually beneficial.

The process 16a was experimentally tested. All experiments are conducted on a dynamic cardiac MRI dataset, which is collected from 25 volunteers and three of them are diagnosed with cardiac dyssynchrony disease. It contains 4,000 2D slices of SAX images with manually annotated LV contours over various spatial locations and cardiac phases.

TABLE 1

| Method | RMSE↓ 50% | PSNR↑ 50% | RMSE↓ 25% | PSNR↑ 25% |
| --- | --- | --- | --- | --- |
| L1-wavelet [14] | 0.0680□0.0 | 23.5844□2.0 | 0.0975□0.0 | 20.6242□2.7 |
| Total variation | 0.0713□0.0 | 23.1699□2.0 | 0.0908□0.0 | 21.0009□1.6 |
| Low-rank [10] | 0.0508□0.0 | 26.2022□2.4 | 0.1014□0.0 | 20.2634□2.7 |
| RU-Net | 0.0331□0.0 | 29.1018□1.9 | 0.0546□0.0 | 24.0784□1.4 |
| FR-Net-2D | 0.0225□0.0 | 32.8431□2.3 | 0.0430□0.0 | 26.5066□1.6 |
| FR-Net- | 0.0220□0.0 | 33.0129□2.2 | 0.0411□0.0 | 26.9550□1.7 |
| Joint-FR-2D | 0.0236□0.0 | 32.3520□2.3 | — | — |
| Joint-FR- | 0.0241□0.0 | 32.3455□2.1 | — | — |

Figure 3A:
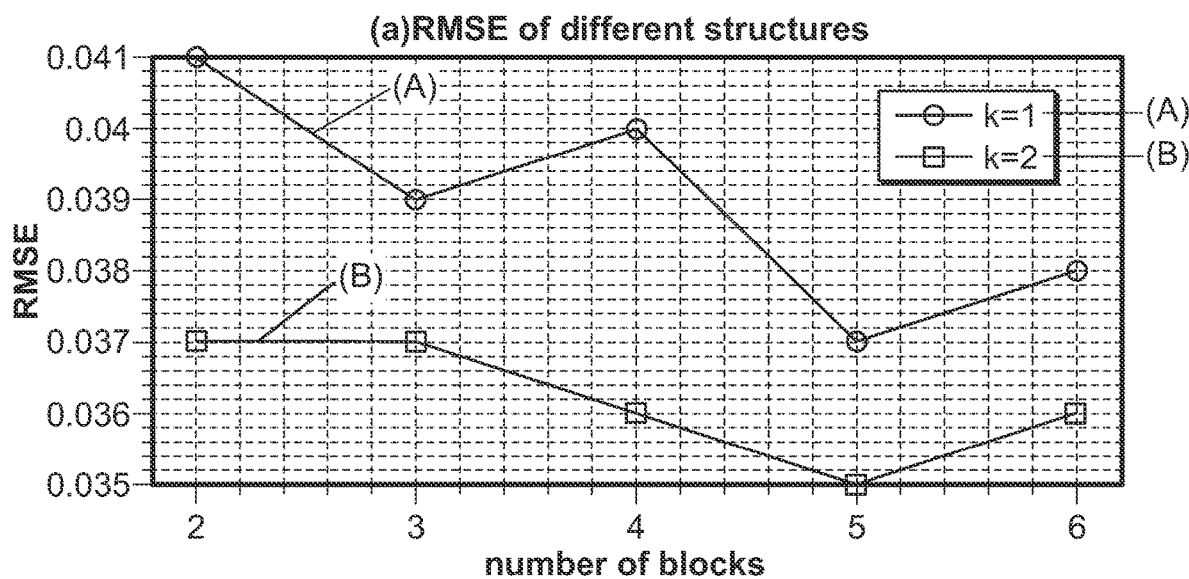
FIGS. 3A-3B are graphs illustrating the RSME of different structures (FIG. 3A) as well as the training time of different structures (FIG. 3B)
Figure 3B:
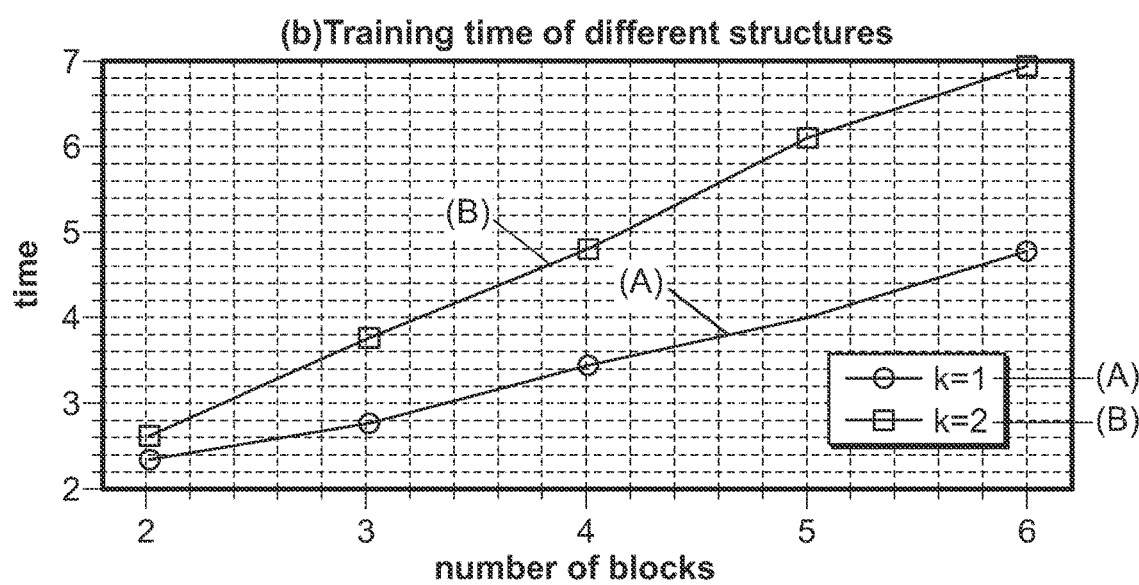

FIGS. 3A-3B are graphs illustrating reconstruction results with k-space data at undersampled rate 25%.

Conventional MRI segmentation approaches consist of two separate steps. Basically, the first step is to reconstruct an image from undersampled k-space data and the second step is to feed the reconstructed image into an established segmentation model using automatic methods. For simplicity, we call this conventional approach Two-step Model. We propose a joint model called Joint-FR-Net. As shown in FIG. 1, Joint-FR-Net is an end-to-end deep neural network, which takes k-space data as input and directly learns segmentation mask as output. One significant difference from Two-step Model is that the "reconstructed image" is now a set of differentiable parameters that connect FR-Net 24 and U-Net 28. The motivation behind this change is to bridge the gap We randomly sample ⅔ of the 25 subjects as the training set and the rest ⅓ as the test set. We apply Fourier transform to convert SAX image to k-space data and undersample it. Particularly, we keep eight lowest spatial frequencies and adopt Cartesian un-dersampling on k-space data along phase direction. Then undersampled k-space data can be simulated. Our model is assessed on the data at undersampled rates of 25% and 50%. Since the dataset is a dynamic sequence of SAX images, we consider both the 2D case and 2D+time case in the following experiments. In the reconstruction task, we quantitatively evaluate our method by root-mean-square error (RMSE) and peak signal-to-noise ratio (PSNR). In the segmentation task, we choose the commonly-used Dice's score and average perpendicular distance (APD) as our measure.

As shown in FIG. 2, we initialize $x_0$ by Fourier transform on the k-space data. The number of steps (k) and the number of blocks between each step (n) are unknown and there could be infinite combinations. Therefore, we run an empirical experiment to decide the structure of the FR-Net. FIGS. 3A-3B show the corresponding RMSE and training time of different structures. We train different structures with undersampled data at rate of 50% and only run 15 epochs. Specifically, the line k=1 means there is only one step, $x_0$ and $x_1$. The line k=2 means there are two steps $x_0$, $x_i$ and $x_2$. We increase the number of blocks between each step and see how their RMSE changes. Balancing between time efficiency and reconstruction quality, we choose five blocks respectively between $x_0$ and $x_1$, $x_1$ and $x_2$ (k=2). $X_2$ is the output of reconstructed image.

We compare our model with both CS-based methods and the state-of-the-art deep learning approach. Specifically, we consider following three classic CS-based methods with different regularization terms: $\ell_1$-wavelet, the total variation approach, and the low-rank approach. We also consider one deep learning approach called RU-Net that is a variation of U-Net. Both FR-Net and RU-Net are implemented in PyTorch and trained with ADAM optimizer on Tesla K80. In order to further improve the performance, we also adopt a k-space correction strategy by replacing zeros of the original k-space data with the values of the reconstructed image that in k-space. The average results are reported in Table 1, above. As we can see, our FR-Net-2D model achieves the best performance. And it also outperforms RU-Net in two cases with the lowest RMSE 0.0225 and 0.0430 respectively. For 2D+time data, we use 5 successive frames as input. The results show that the FR-Net-2D+time model which performs on dynamic data, achieves the best performance in terms of RMSE and PSNR in both cases. This validates that our model performs very well at different undersampled rates with and without temporal information.

Figure 4:
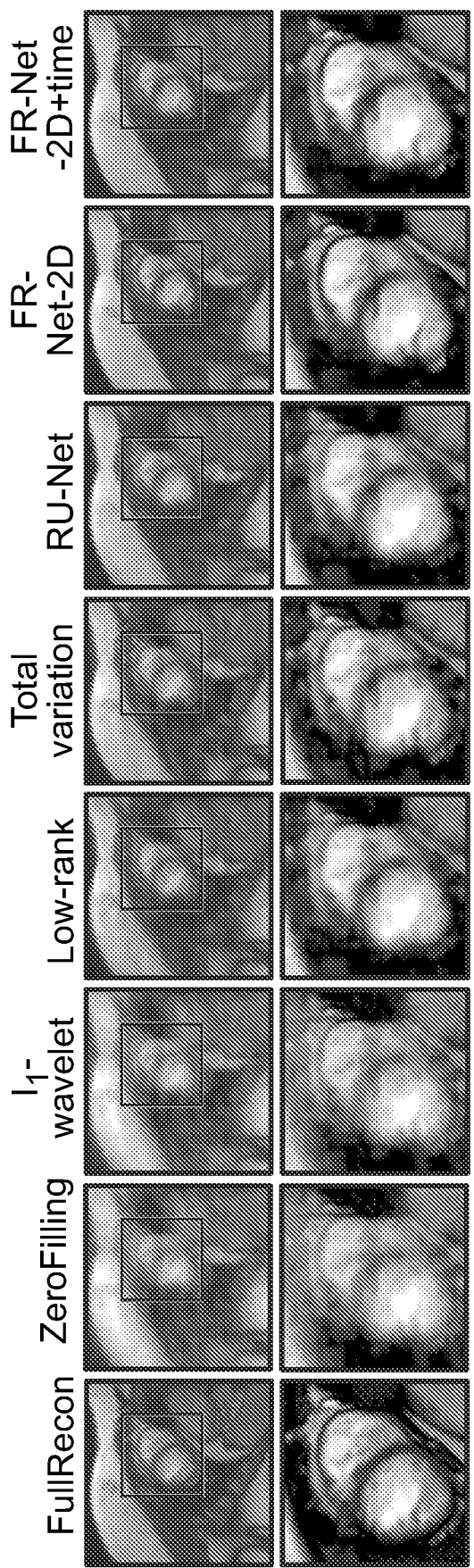
FIGS. 4-5 illustrate operation of the processing step 16a of the system.

FIG. 4 shows the reconstruction results at different undersampled rates. As we can see, the CS-based methods miss lots of details and the reconstructed images are blurry and fuzzy. In contrast, deep learning methods are more precise and efficient. Specifically, our FR-Net 2D and FR-Net 2D+time models yield much clearer and high-quality images.

Table 2, below, shows average endo- and epicardium segmentation performance of test set. The input k-space data is at undersampled rate 50%.

dynamic data and we call them Joint-FR-2D and Joint-FR-2D+time in this experiment. The training and test data are based on the undersampled rate of 50%. Experiments are conducted on both endo- and epicardium segmentation. The average segmentation results are reported in Table 2 above. We observe that our two joint models outperform the Two-step model in terms of Dice and APD for both endo- and epicardium cases. The Two-step model only gains 0.6635 and 0.7494 Dice score in endo. and epi. case, respectively. We also find that the Joint-FR-2D+time model achieves better results than the Joint-FR-2D model. This highlights the generalization ability of our model to dynamic data. Moreover, we can see the Dice index of Joint-FR-2D+time model is very close to that of fully-sampled model. The reconstruction performance of the Joint-FR-2D and Joint-FR-2D+time models are also reported in Table 1. It achieves comparable results with the FR-Net-2D and FR-Net-2D+time models and outperforms other CS-Based methods. Thus, we conclude that our joint model not only benefits the segmentation task but also achieves promising reconstruction results compared with the other CS-based models. We also plot the segmentation results in FIG. 5. Note that for better visualization, we use fully-sampled image as reconstructed image here. As the Joint-FR-Net models are trained with the raw k-space data, they compute similar contours to the ground truth.

Figure 6:
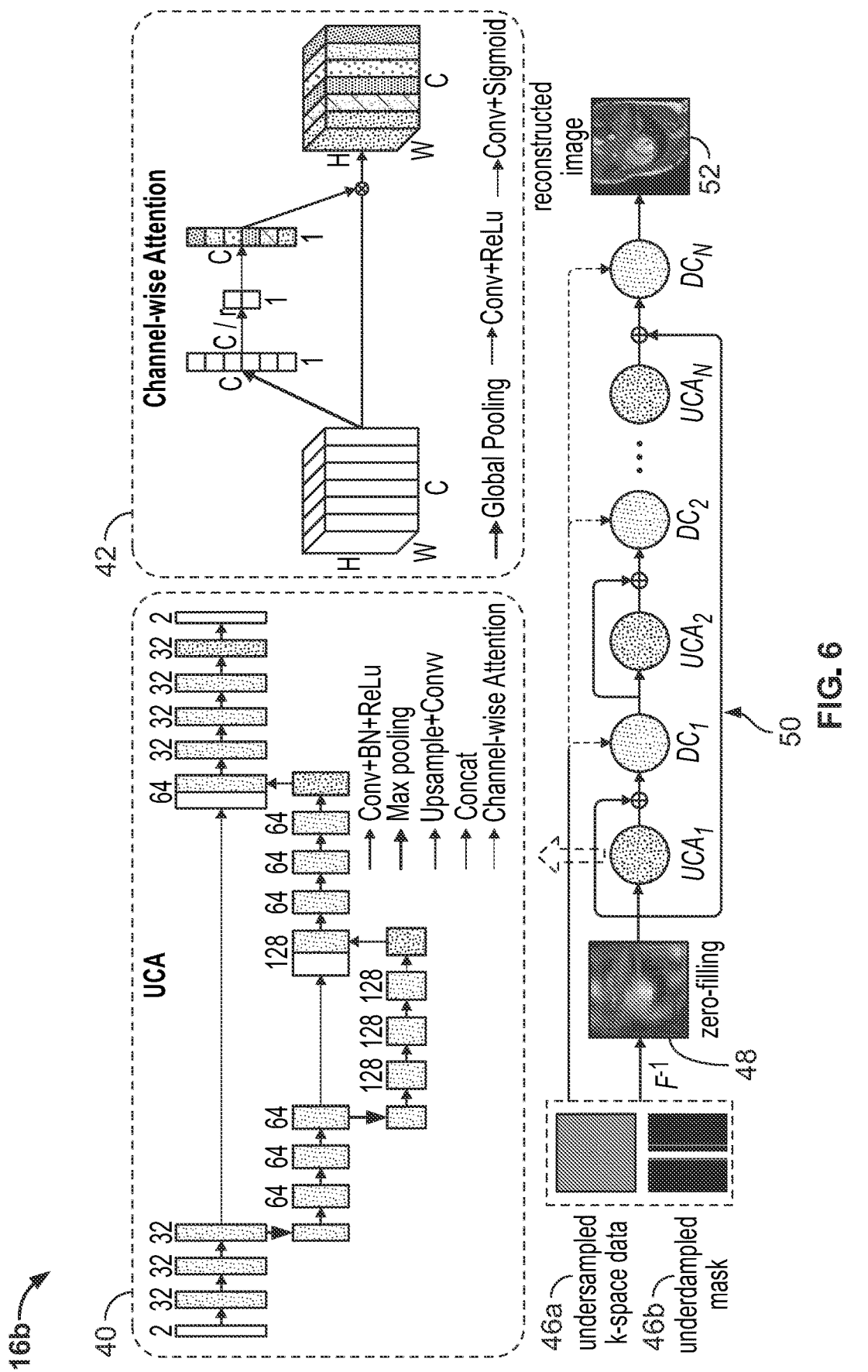
FIG. 6 is a diagram illustrating processing performed by step 16b of FIG. 1, in greater detail.

FIG. 6 is a diagram illustrating processing performed by step 16b of FIG. 1, in greater detail. By way of background, in Compressed Sensing (CS)-based MRI reconstruction problems, the goal is to find a reconstructed image $\tilde{x}$ such that it minimizes the reconstruction error between original k-space data y and Fourier transform of x:

$$\tilde{x} = \mathrm{argmin}_x \|F_u(x) - y\|_2^2 + R(x). \tag{1}$$

Here $F_u$ is an operator that transforms x into Fourier domain with undersampling. R(•) is a regularization term that depends on the prior information of data and general choices are $\ell_1$ or $\ell_0$.

Traditionally, the objective function of Equation 1 immediately above is solved in an iterative manner that requires thousands of iteration steps until convergence. A more efficient way is to approximate the optimal reconstructed image from undersampled k-space data via deep neural

TABLE 2

| Method | Dice↑ | ADP(mm)↓ | Dice↑ | ADP(mm)↓ |
|---|---|---|---|---|
| | Endo. | | Epi. | |
| Fully-sampled | 0.7661 ± 0.2658 | 4.1774 ± 5.0946 | 0.7754 ± 0.2677 | 5.7527 ± 10.8612 |
| Zero-filling | 0.6357 ± 0.3009 | 7.7575 ± 10.9018 | 0.6570 ± 0.3040 | 9.8359 ± 15.0050 |
| Two-step | 0.6635 ± 0.3081 | 9.1255 ± 21.1796 | 0.7494 ± 0.2734 | 8.2817 ± 18.4909 |
| Joint-FR-2D | 0.7260 ± 0.2787 | 4.9771 ± 5.7992 | 0.7503 ± 0.2922 | 6.9593 ± 12.3803 |
| Joint-FR-2D + time | 0.7310 ± 0.2603 | 4.2884 ± 4.9119 | 0.7573 ± 0.2763 | 1.2628 ± 1.6988 |

Figure 5:
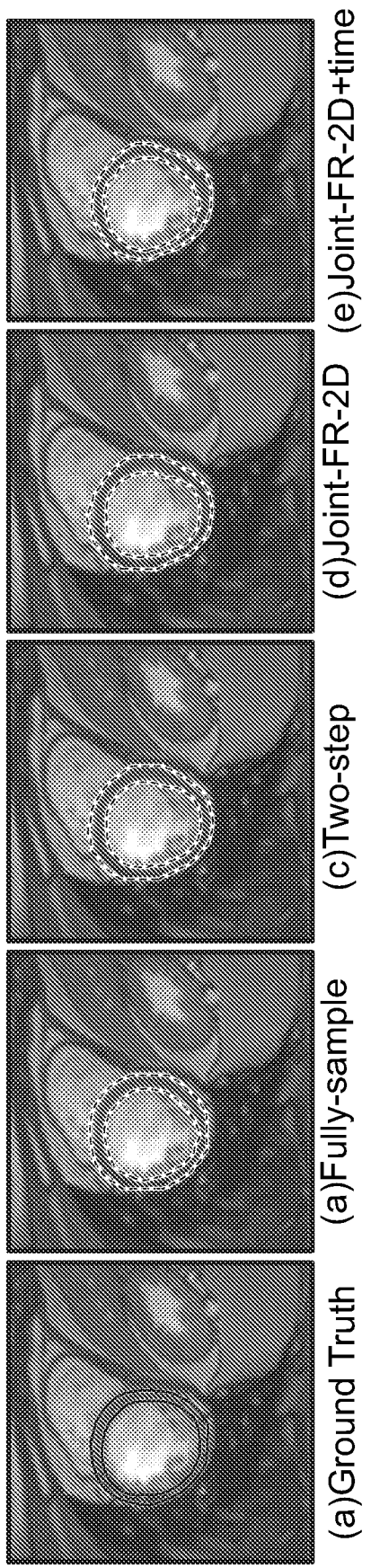

FIG. 5 shows segmentation results of input data is at undersampled rate 50%. In this experiment, we train a U-Net with fully-sampled images and use it as the best achievable model. We also train another model with zero-filling images as the lower bound of segmentation performance. In order to show the mutual benefits of the Joint-FR-Net on solving the myocardium segmentation problem. We compare our method with the Two-step model which takes as input the images reconstructed from the FR-Net. Our method respectively takes as input the 2D k-space data and the 2D+time network. One issue is that as the network goes deeper, the original information may be degraded. A Data Consistency (DC) layer can be used to avoid loss of information. Basically, DC layer takes as input the reconstructed image $x_n$ from the n-th reconstruction block and outputs an updated "reconstructed" image $x^{dc}_n$. Formally, DC layer is defined as $$x_n^{dc} = DC(x_n) = F^H(\tau(F(x_n))). \tag{2}$$

Here F(x) is Fourier transform that takes image x as input and outputs $\hat{x}$ in Fourier domain and $F^H(x)$ is inverse Fourier transform. τ(x) is the data fidelity operation whose output has the same dimension as $\hat{x}$:

$$\tau(\hat{x})[i,j] = \begin{cases} \hat{x}[i,j], & (i,j) \notin \Omega \\ \dfrac{\hat{x}[i,j] + vy[i,j]}{1+v}, & (i,j) \in \Omega \end{cases} \qquad (3)$$

where [i,j] is the matrix indexing operation, $\Omega$ is the set of sampled positions of k-space data and $v \in [0, \infty)$ is the noise level. In the noiseless case ($v \to \infty$), we have $\hat{x}[i,j] = y[i,j]$ if $(i,j) \in \Omega$, i.e. filling $\hat{x}$ with the original values of k-space data y at position (i,j).

The process 16b is shown in greater detail in FIG. 6 and is referred to herein as MR Cascaded Channel-wise Attention Network (MICCAN). As shown in FIG. 6, MICCAN mainly consists of two parts: U-net with Channel-wise Attention (UCA) modules 40, 42 and DC layer 50. These components are cascadedly coupled together and repeat for N times. Formally, denote the n-th UCA module 40 and the n-th DC layer 50 respectively by $UCA_n$ and $DC_n$. The starting point of MICCAN is undersampled k-space data y (elements 46a, 46b) which is later converted into a zero-filling image (element 48) $x_0 = F^H(y)$ through inverse Fourier transform $F^H$ and fed to a UCA module 40. The reconstructed image 52 is produced by the module 40. Our cascaded model can be simply formalized as $$\begin{cases} x_n = UCA_n(x_{n-1}^{dc}) + x_{n-1}^{dc} \\ x_n^{dc} = DC_n(x_n) \end{cases} (n = 1, \ldots, N) \qquad (4)$$

where $x_0^{dc}$ is initialized as $x_0$. The final reconstructed image of MICCAN, namely $x_N^{dc}$, is produced by the last DC layer ($DC_N$).

In the previous work on reconstruction problem, deep learning based methods have two major issues. First, they treat each channel-wise feature equally, but contributions to the reconstruction task vary from different feature maps. Second, receptive field in convolutional layer may cause to lose contextual information from original images, especially high-frequency components that contain valuable detailed information such as edges and texture. We developed the UCA module by introducing an attention mechanism that filters the useless features and enhance the informative ones. The attention technique is only applied in the decoder part. The intuition is that features of the decoder are extracted from coarse to fine feature-maps of multiple scales via skip connection. The attention module filters salient and prunes irrelevant and noisy features such that allows model parameters in shallower layers to be updated mostly that are relevant to a given task.

Specifically, we use global average pooling to extract the channel-wise global spatial information to vector $z \in \mathbb{R}^C$, whose c dimension is defined as $$z_c = \frac{1}{H \times W} \sum_{i=1}^{H} \sum_{j=1}^{W} f_c[i,j] \{c = 1, \ldots, C\} \qquad (5)$$

where $f_c \in \mathbb{R}^{W \times H}$ is the feature map in the c-th channel. Such operation squeezes the spatial information of the whole image into a vector length of C. To further extract feature related to the final task, we introduce another gating mechanism as follows:

$$\hat{x}_c = \sigma(\delta(z * W_1) * W_2) \odot f_c, \qquad (6)$$

where "*" is convolution operator and $\delta(\bullet)$ is ReLU activation function to encode the channel-wise dependencies. $W_1$ is a kernel in the first convolutional layer that reduces the C-dimensional feature vector into C/r. On the contrary, kernel W2 increases feature size back to C. Sigmoid function $\sigma(\bullet)$ is used to compute weighted attention map, which is later applied to rescaling the input feature $f_c$. Based on this attention mechanism in the UCA module, our model MICCAN achieves very promising results and outperforms several state-of-the-art methods.

The end-to-end network consists of UCA blocks 40, Data Consistency blocks 50, and Channel-wise Attention units 42. It takes as input the undersampled k-space data 46a and the undersampled mask 46b (leftmost) and outputs the reconstructed MRI image 52 (right-most image). The zero-filled reconstruction image 48 (second-left image) works as the start point for reconstruction. The Data Consistency unit 50 employs the original k-space data 46a for further refinement.

To address the problem of vanishing low frequency in deep learning based MRI reconstruction, we utilize a long skip connection from the zero-filling image to the final reconstruction block. Specifically, we replace the residual in the last UCA module, namely $X_N = UCA_N(X^{dc}_{N-1}) + x^{dc}_{N-1}$, with a long skip connection:

$$x_N = UCA_N(x_{N-1}^{dc}) + x_0 \qquad (7)$$

This simple modification is used to learn the global residual and to stabilize the gradient flow in deep residual network.

A common choice of loss function for reconstruction problems is $\ell_2$, but the resulting reconstructed image is of low quality and lacks high frequency detail. Therefore, we propose to use a combination of loss functions including $\ell_1$ loss and perceptual loss $\ell_p$. Given target image $x_s$ and reconstructed image $x = x^{dc}_N$ of MICCAN parameterized by $\theta$, the combined loss is defined as $$\ell^\theta(x, x_s) = \lambda_1 \ell_1^\theta(x, x_s) + \lambda_p \ell_p^\theta(x, x_s) \qquad (8)$$

where $$\ell_1^\theta(x, x_s) = \|x - x_s\|_1 \qquad (9)$$

$$\ell_p^\theta(x, x_s) = \sum_{k=1}^{K} \|\phi_{VGG}^k(x) - \phi_{VGG}^k(x_s)\|_2^2 \qquad (10)$$

where $\lambda_1$ and $\lambda_p$ are weighing factors for two losses, $\Phi kVGG(\bullet)$ represents features of the k-th activation layer in VGG network. Note that perceptual loss $\ell_p$ minimizes the $\ell_2$ distance between reconstruction image and target image in K different feature spaces, or equivalently it encourages the predicted image to be perceptually similar to the target image.

To evaluate the effectiveness of process 16b, we compare it with several state-of-the-art approaches on a simulated cardiac k-space dataset. We evaluate following methods in the experiment. Two traditional CS-MRI methods include $\ell$ 1-wavelet and TV norm, which are implemented in the BART toolbox. Two deep learning based models include DC-CNN and MRN5. The only difference between our proposed MICCAN and MRN5 is that MRN5 does not used attention module and long skip connection. We also consider three variants of our methods: MICCAN with $\ell_2$ loss (MICCAN-A), MICCAN with combined loss (MICCAN-B), and MICCAN with both long skip connection and combined loss (MICCAN-C). We set the reduction ratio r as 8 for all our MICCAN models. For the combined loss, we set $\lambda_1$ as 10 and $\lambda_p$ as 0.5. As the shallow features encode details of images, we compute the perceptual loss of layer relu1-2, relu2-1, relu2-2 and relu3-1 of the VGG-16 network. All deep learning models are implemented using PyTorch and trained on NVIDIA K80. Learning rate is initialized as $10^{-4}$ with decreasing rate of 0.5 for every epochs. The training batch is 8 and the maximum number of epochs is 50. For fair comparison, we set the number of reconstruction blocks N as 5.

Figure 7:
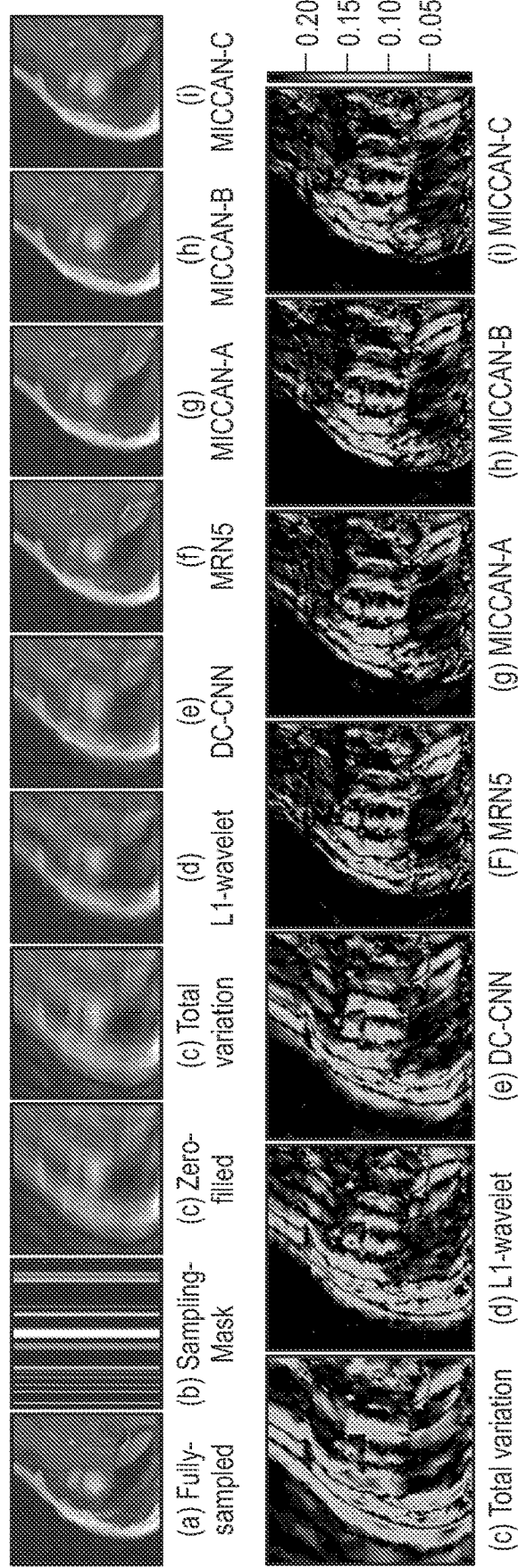
FIG. 7 illustrates operation of the processing step of 16b of the system.

FIG. 7 illustrates wisualization of reconstructed images and reconstruction errors with k-space data at undersampled rate 12.5%. Also, Table 3, below, shows reconstruction results of the proposed MICCAN models and other methods.

TABLE 3

| Methods | NRMSE | PSNR | SSIM |
| --- | --- | --- | --- |
| TV | 0.1087 ± 0.0 | 19.7388 ± 2.8 | 0.5923 ± 0.0 |
| i1-wavelet | 0.0753 ± 0.0 | 22.7054 ± 2.0 | 0.6333 ± 0.0 |
| DC-CNN | 0.0587 ± 0.0 | 24.7993 ± 1.7 | 0.6612 ± 0.0 |
| MRN5 | 0.0427 ± 0.0 | 27.5373 ± 1.5 | 0.7851 ± 0.0 |
| MICCAN | 0.0402 ± 0.0 | 28.0664 ± 1.6 | 0.8005 ± 0.0 |
| MICCAN | 0.0391 ± 0.0 | 28.3283 ± 1.7 | 0.8214 ± 0.0 |
| MICCAN | 0.0385 ± 0.0 | 28.4489 ± 1.6 | 0.8198 ± 0.0 |

A cardiac MRI dataset with 15 subjects is adopted in our experiments. We randomly choose 10 subjects as training set, 2 subjects as validation set and the rest 3 subjects as test set. We follow the k-space data simulation method. It assumes the sampled mask follows a zero-mean Gaussian distribution and the Cartesian undersampling method is adopted, also keeps the eight lowest spatial frequencies. Our model is evaluated on data with undersam-pled rate at 12.5% (acceleration rate 8×).

We also quantitatively evaluate all models with three widely used measurements: normalized root square mean error (NRMSE), peak signal-to-noise ratio (PSNR) and the structural similarity index measure (SSIM). The results are shown in Table 3 and we basically observe following three trends. First, all our MICCAN variants outperform other baseline models. This mainly attributes to the attention mechanism. Even trained with £2 loss, MICCAN-A achieves NRMSE of 0.0402, PSNR of 28.0664 and SSIM of 0.8005 that beats MRN5 model. Second, MICCAN-B model that is trained with combined loss gains better result than MICCAN-A. For example, MICCAN-B has 2.7% decrease in NRMSE compared with MICCAN-A and also achieves the best SSIM value of 0.8214. This indicates that our combined loss is better than the £$_2$ loss, making image less blur and keeping the perceptual details. Third, with long skip connection, MICCAN-C further improves reconstruction performance with the lowest NRMSE of 0.0385 and the highest PSNR value of 28.4489. Overall, all these results demonstrate the effectiveness of the channel-wise attention modules and the proposed combined loss.

We further visualize the reconstructed image and reconstruction errors on a test sample and qualitatively analyze the results of all methods. As shown in FIG. 7, most of the baseline methods cannot completely recover detail of the image and suffer from severe blurring artifacts. In contrast, our three MICCAN methods eliminate most blurring artifacts and recover more details from low undersampled k-space data. Furthermore, for the transitional methods such as £$_1$-wavelet and TV, the reconstructed images are similar to the zero-filling image and suffer from heavy blurring artifacts. We highlight that our MICCAN achieves best results and with much fewer reconstruction errors.

Figure 8:
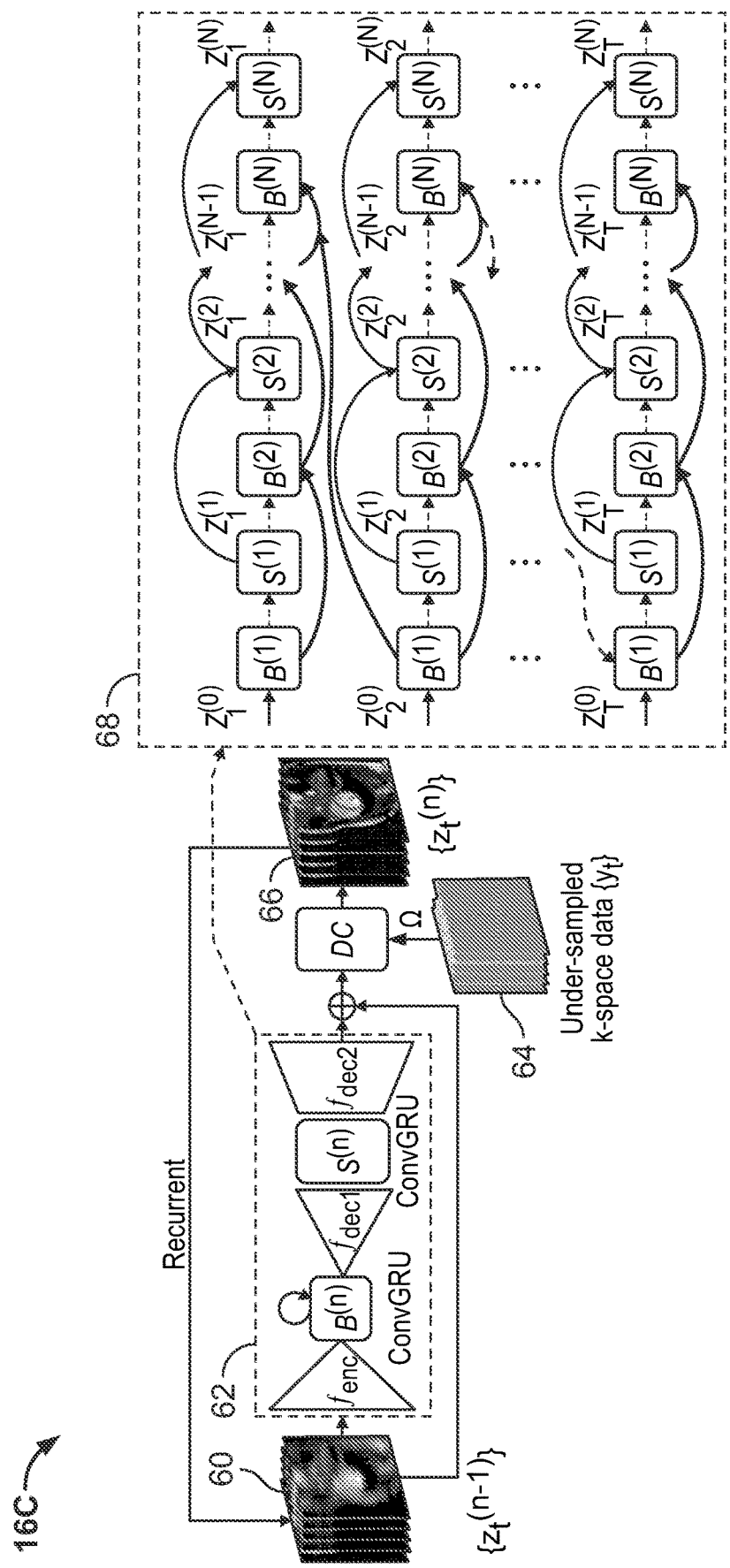
FIGS. 8-9 are diagrams illustrating processing performed by step 16c of FIG. 1, in greater detail.
Figure 9:
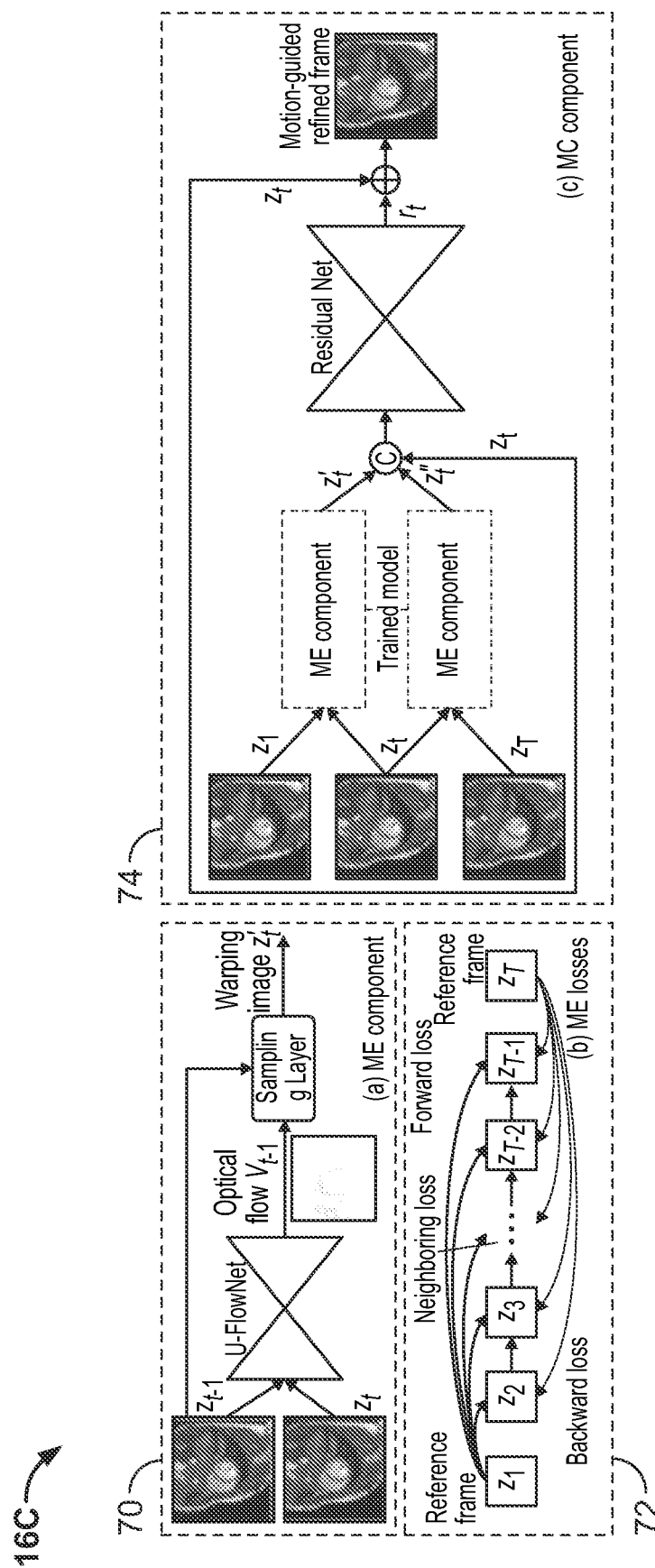

FIGS. 8-9 are diagrams illustrating processing performed by step 16c of FIG. 1, in greater detail. The following framework is provided in connection with step 16c. Given a sequence of under-sampled k-space data $\{yt\}_{t \in [T]}$ of T frames, the dynamic MRI reconstruction problem is to predict reconstructed images $(zt)_{t \in [T]}$ from $\{y_t\}$, which can be formalized as an optimization problem: $\text{argmin}_{\{z_t\}} L_{rec}$ $(\{z_t\})$, where:

$$\mathcal{L}_{rec}(\{z_t\}) = \sum_{t=1}^{T} \frac{1}{2} \|F_u(z_t) - y_t\|_2^2 + \lambda R(z_t). \quad (1)$$

The term $\|F_u(z_t) - y_t\|^2_2$ is used to guarantee data consistency by restricting the reconstructed image z, to be close to the input measurement $y_t$. $F_u(\bullet)$ is an operator that transforms image-domain zt into Fourier domain followed by undersampling. $R(\bullet)$ is a regularization function that depends on the prior knowledge of the input $\{y_t\}$. Common choices include sparsity in transformed domain, total variation (TV) penalties, and low-rank property. $\lambda$ is a weighting factor.

In order to capture anatomical motion in the dynamic MRI acquisition, it is natural to incorporate motion estimation/motion compensation (ME/MC) technique in the reconstruction process. Specifically, based on the brightness constancy assumption, for a temporal 2D image $z_t(x, y, t)$ with small movement $(\Delta x, \Delta y, \Delta t)$ with respect to the next frame, we add the following motion estimation constraint to the objective function (1):

$$\mathcal{L}_{me}(\{v_t\}) = \sum_{t=1}^{T-1} \left\| \nabla z_t^T v_t + \frac{\partial z_t}{\partial t} \right\|_1 + \delta \|v_t\|_1, \quad (2)$$

where $$\nabla z_t(x, y) = \left( \frac{\partial z_t}{\partial x}, \frac{\partial z_t}{\partial y} \right)$$

are the derivatives of image $z_t$ at position (x,y), and $$v_t(x, y) = \left( \frac{\Delta x}{\Delta t}, \frac{\Delta y}{\Delta t} \right)$$

is the estimated displacement motion fields or optical flow.

Furthermore, given the estimated motion field $v_t$, the reconstructed image $z_t$ can be re-fined through MC process, i.e. $c_t = MC(z_t, z_1, z_T) + r_t$, where $c_t$ is the motion-compensated reconstructed image and $r_t$ is a residual term for better exploiting temporal redundancy. Therefore, we can derive the motion compensation constraint as follows.

$$\mathcal{L}_{mc}(\{r_t\}) = \sum_{t=1}^{T-1} \frac{1}{2} \|F_u(c_t) - y_t\|_2^2. \quad (3)$$

By combining with two motion-based constraints of Equations (2) and (3) immediately above, the motion-guided dynamic MRI reconstruction problem is defined as:

$$\underset{\{z_t, v_t, r_t\}}{\mathrm{argmin}} \mathcal{L}_{rec}(\{z_t\}) + \eta \mathcal{L}_{me}(\{v_t\}) + \zeta \mathcal{L}_{mc}(\{r_t\}). \tag{4}$$

The solution to Equation (4) immediately above is non-trivial and traditional CS-based algorithms are usually computationally expensive and require long running time for hyper-parameter tuning. Recent advances in deep learning provide an alternative way for efficient MRI reconstruction, but very few works focused on the dynamic reconstruction problem and they only targeted for the simpler Equation (1) immediately above without considering motion information. To this end, we propose a deep learning based method called Motion-guided Dynamic Reconstruction Network ("MODRN") to solve Equation (4) immediately above.

Process 16c separates the motion-guided dynamic reconstruction problem into three closely-connected parts: (i) Dynamic Reconstruction (DR) component for estimating initial reconstructed image from Equation (1) immediately above; (ii) Motion Estimation (ME) component for generating motion information through Equation (2) immediately above; and (iii) Motion Compensation (MC) component for refining reconstructed image guided by learned motion based on Equation (3) immediately above.

Instead of directly solving Equation (1) immediately above, an iterative process is adopted through DR component to approximate reconstructed images $z_t$. Formally, given under-sampled k-space data $\{y_t\}_{t \in [T]}$ with sampled mask $\Omega$, DR component learns to reconstruct images in N iterations:

$$z_t^{(n)} = DR(z_t^{(n-1)}, y_t, \Omega) \Leftrightarrow \begin{cases} x_{bt}^{(n)}, b_t^{(n)} = B(f_{enc}(z_t^{(n-1)}), b_t^{(n-1)}) \\ x_{st}^{(n)}, s_t^{(n)} = S(f_{dec1}(x_{bt}^{(n)}), s_t^{(n-1)}) \\ z_t^{(n)} = DC(f_{dec2}(x_{st}^{(n)}) + z_t^{(n-1)}, y_t, \Omega) \end{cases}, \tag{5}$$

$n \in [N]$.

where $z_t^{(0)}$ is zero-filling image and $z_t^{(n)}$ is the reconstructed image of $y_t$ after iteration n. B and S are two ConvGRU units that respectively output features $x_{bt}^{(n)}$ and $x_{st}^{(n)}$ together with hidden states $b_t^{(n)}$ and $s_t^{(n)}$. $f_{enc}$ and $f_{dec1}$, $f_{dec2}$ are convolutional encoder and decoders in the U-Net, which is used as the backbone of the DR component to capture course-to-fine features of reconstructed images. Equation (5) immediately above is visualized in FIG. 8 for better understanding.

As can be seen in FIG. 8, process 16c includes input data 60, recurrent processing steps 62, under-sampled k-space data 64, intermediate data 66, and final processing steps 68. One benefit here is that regularization function R(•) in Equation (1) immediately above is now built upon the convolutional network for automated feature learning and hence avoid the requirements of prior knowledge on the selection of R. DC(•) is the differentiable DC layer that takes the same effect as the data consistency term $\|Fu(z_t) - y_t\|_2^2$ in Equation (1) immediately above to force the reconstructed image to be consistent with the input data. It fills the reconstructed image $z_t$, with the original values of input data $y_t$ in the Fourier domain by the sampled mask $\Omega$.

In order to capture dynamic information of image sequence during each iteration, two kinds of ConvGRU units are introduced in recurrent processing steps 62, namely, B and S, inspired by Equation (5) immediately above. The difference between B and S is that GRU unit S is used to improve the performance of image $z_t$ over N iterations while the role of B is to connect dynamic information of neighboring images $z_{t-1}$ and $z_t$, which is implemented by initializing hidden state $b_t^{(0)}$ as $b_{t-1}^{(N)}$. Finally, we impose $l_1$ on the reconstructed images $\{z_t^N\}$ with respect to ground truth for penalizing In analogy to Equation (2) immediately above, the Motion Estimation (ME) component takes as input the sequence of reconstructed images $\{zt\}_{t \in [T]}$ and learn to predict displacement motion fields $\{vt\}_{t \in [T]}$. As shown in FIG. 9, our proposed ME component embraces two parts: a FlowNet backboned by convolutional U-Net (U-FlowNet) 70 for motion field estimation. The other is a differentiable sampling layer 72 based on Spatial Transformer Network (STN), which endows convolutional network with the ability to warp the spatial deformation between images. Unlike traditional optimization algorithms for motion estimation that depend on a strong assumption that the brightness of two fames should be consistent and the movement of the foreground object is small, our method does not succumb to any assumption and hence is more applicable in practical dynamic MRI reconstruction. The performance of ME is heavily affected by noisy input, therefore it is pre-trained with two fully sampled images $z_{t-1}$ and $z_t$. The image pair is first fed to the U-FowNet 70, which produces two-channel displacement $v_{t-1}$ along the x and y directions. Then, the sampling layer warps $z_{t-1}$ towards $z_t$ by using $v_{t-1}$ and yields a warping image denoted by $z_t^0$ through differentiable bilinear interpolation. This leads to a natural re-formalization of motion estimation (ME) loss $\ell_{me}$ between $z_{t-1}$ and $z_t$ from Equation (2):

$$\ell_{me}(z_{t-1}, z_t) = \|z'_t - z_t\|_1 + \beta \|v_{t-1}\|_1 + \gamma \|v_{t-1}\|_{TV}. \tag{6}$$

The first term is an image reconstruction loss used to keep the majority of high-frequency parts on images. Two additional regularization terms reinforce constraints on the motion field $v_{t-1}$, where $l_1$ regularization is to suppress unreal large magnitude of displacement and total-variation (TV) regularization is to make the displacement locally smooth.

In addition, the above loss only enforces temporal consistency between consecutive frames, but there is no guarantee for long-term coherence. Therefore, we consider to train the U-FlowNet 70 with three sets of ME losses to capture long-term motion information, as illustrated in FIG. 9.

$$\mathcal{L}_{me}(\{z_t\}) = \sum_{t=2}^{T-1} \ell_{me}(z_1, z_2) + \sum_{t=2}^{T-1} \ell_{me}(z_t, z_T) + \sum_{t=2}^{T-2} \ell_{me}(z_t, z_{t+1}), \tag{7}$$

where three terms on the right-hand-side are respectively forward ME loss, backward ME loss and neighboring ME loss.

Motion Compensated (MC) component is used to refine reconstructed images $\{zt\}_{t \in [T]}$ through motion information and to generate motion compensated image $\{ct\}_{t \in [T]}$. During the MC stage 74 shown in FIG. 9, two additional fully sampled reference frames are added to learn more accurate displacement motion fields. The pre-trained U-FlowNet 70 is fixed and directly used as an operator in the MC stage 74. As shown in FIG. 9, the MC stage 74 takes a reconstructed image $z_t$ from the DR component and two reference frame $z_1$ and $z_T$ as input. It first retrieves two warping images $z'_t$ and $z''_t$ from the ME stage 74 by feeding $z_1$, $z_t$ and $z_t$, $z_T$ respectively. These two images represent forward and backward motion information, which is then concatenated and fed to a residual network to generate residual information $r_t$, as described in Equation (3) immediately above. Finally, the reconstructed image $z_t$ together with the residual $r_t$ are summed up to generate the motion-guided refined image $c_t$, which is penalized by $l_1$ loss with respect to the ground truth image.

An experiment was conducted with a short-axis (SAX) cardiac dataset composed of 15 patients. Each subject contains around 12 SAX planes and each plane includes 24 phases (2D images) that form a whole cardiac cycle. The image resolution is normalized to 1.25 mm and image size is cropped to 152×152 pixels. In order to simulate k-space data, we adopt a Cartesian under-sampling method which assumes that sampled mask Ω follows a zero-mean Gaussian distribution and keeps 8 center spatial frequencies. We consider two different settings on the dataset respectively with under-sampling rates of 20% (or acceleration rate 5×) and 12.5% (8×). For convenience, we refer to these two cases as Rate 5× and Rate 8×. We perform 3-fold cross-validation in the following experiments that each fold contains 10 training subjects and 5 test subjects. Table 4, below, shows the average performance of dynamic MRI reconstruction on the test subjects in both cases of Rate 5× and Rate 8×. The best results are highlighted in bold font.

TABLE 4

| Method | NRMSE↓ 5× | PSNR↑ 5× | SSIM↑ 5× | NRMSE↓ 8× | PSNR↑ 8× | SSIM↑ 8× |
| --- | --- | --- | --- | --- | --- | --- |
| k-t SLR | 0.0934 | 21.0858 | 0.6794 | 0.1054 | 19.9504 | 0.6193 |
| k-t FOCUSS | 0.0766 | 22.7471 | 0.6581 | 0.0879 | 21.4063 | 0.5920 |
| k-t FOCUSS + ME/MC | 0.0758 | 22.8139 | 0.6701 | 0.0854 | 21.6547 | 0.6131 |
| DC-CNN(3D) | 0.0360 | 29.1292 | 0.8449 | 0.0513 | 25.9709 | 0.7441 |
| DRN w/o GRU | 0.0381 | 28.7187 | 0.8286 | 0.0519 | 25.9120 | 0.7448 |
| DRN | 0.0349 | 29.5394 | 0.8502 | 0.0485 | 26.5275 | 0.7687 |
| MODRN | 0.0274 | 32.0403 | 0.9104 | 0.0364 | 29.4774 | 0.8702 |

All of the deep learning models with were implemented with PyTorch and trained on an NVIDIA K80 system. All models are trained for total 80 epochs using Adam optimizer, with initialized learning rate of $5 \times 10^{-4}$ and decreasing rate of 0.5 for every 20 epochs. Due to hardware limitations, the number of iterations is set to be N=3 and the length of image sequence is T=12.

The dynamic reconstruction performance of the proposed methods was evaluated quantitatively and qualitatively in both cases of Rate 5× and Rate 8×. We consider three variants of our models: DRN w/o GRU (the one without GRU hidden unit), DRN (the one with DR component only) and MODRN (the complete version). We compare with four state-of-the-art approaches including k-t SLR, k-t FOCUSS, k-t FOCUSS+ME/MC, and DC-CNN (3D). The first three are traditional CS-based methods and only k-t FOCUSS+ME/MC includes ME/MC procedures. The last one is also a deep learning based method that explores spatio-temporal information using 3D convolution. Three common quantitative metrics are used: root square mean error (NRMSE), peak signal-to-noise ration (PSNR) and structural similarity index measure (SSIM).

The results of all methods are reported in Table 4 above. We observe that all our methods consistently outperform four state-of-the-art approaches in both Rate 5× and Rate 8× cases. In particular, MODRN achieves the best performance for all metrics, mainly attributing to the motion information exploited by ME/MC components. We also find that DRN outperforms DRN w/o GRU by a large margin, which indicates the importance of utilizing dynamic sequence of image.

Figure 10A:
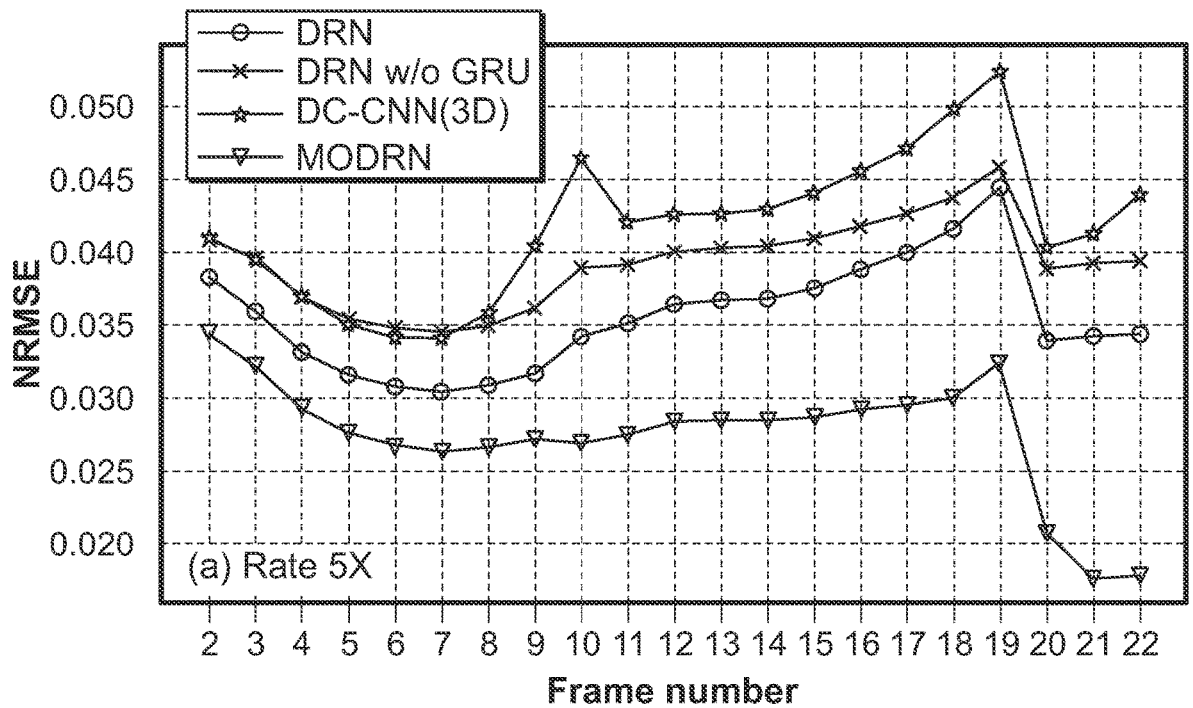
FIGS. 10A-10B are graphs illustrating performance of the process 16c of the system.
Figure 10B:
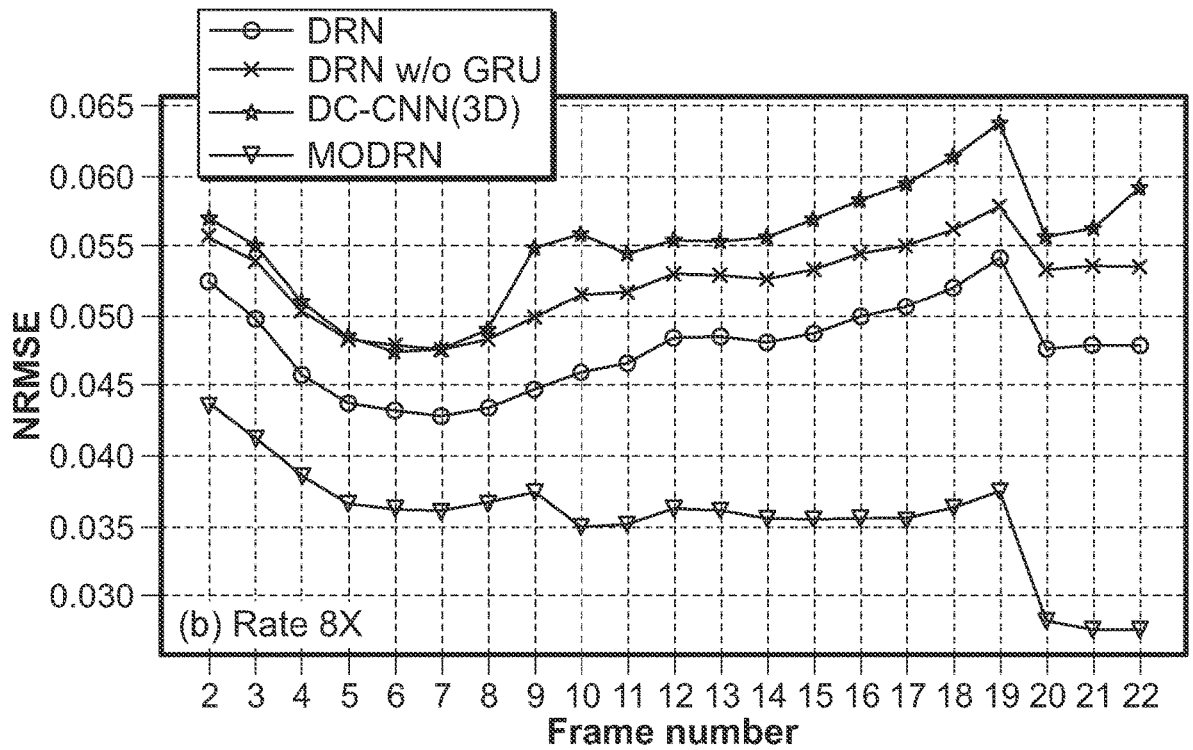

To further investigate the performance of four deep learning methods, we plotted NRMSE values within a complete cardiac cycle of one example in FIGS. 10A-10B. It shows that our method MODRN consistently achieves the smallest error of dynamic reconstruction for the sequence of images. In contrast, the models without ME/MC are unstable along the temporal dimension, especially in the case of DC-CNN (3D). For example, in the case of Rate 8×, the gap between DRN and MODRN model become larger, which implies the significance of using motion information.

Figure 11:
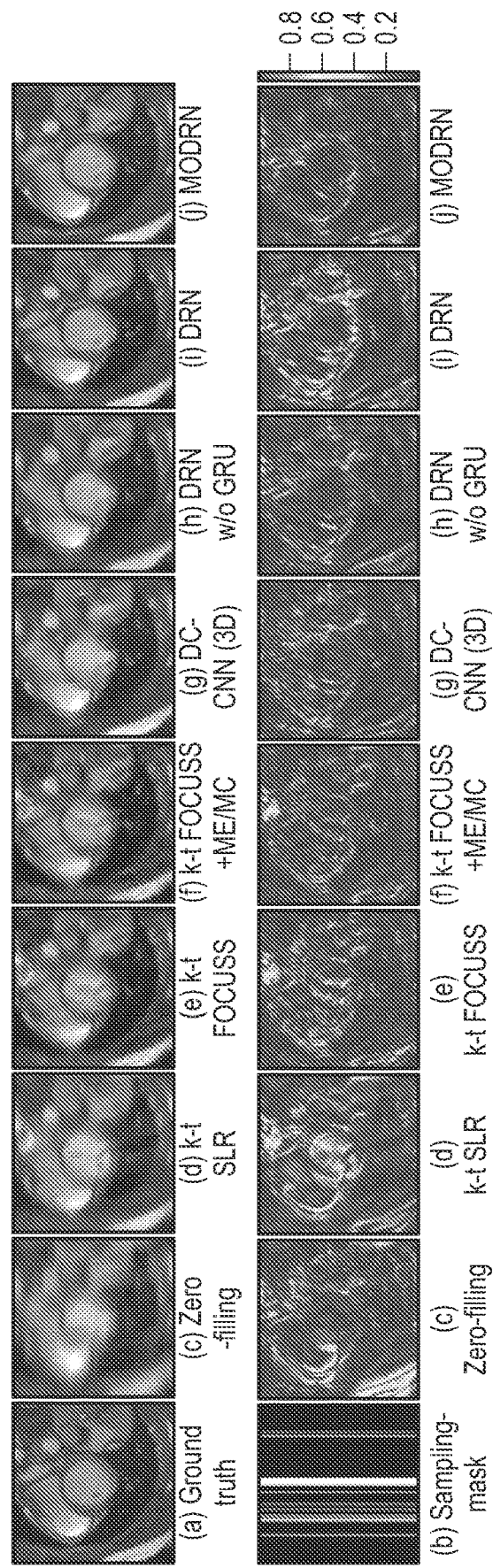
FIGS. 11-12 are images illustrating performance of the process 16c of the system.
Figure 12:
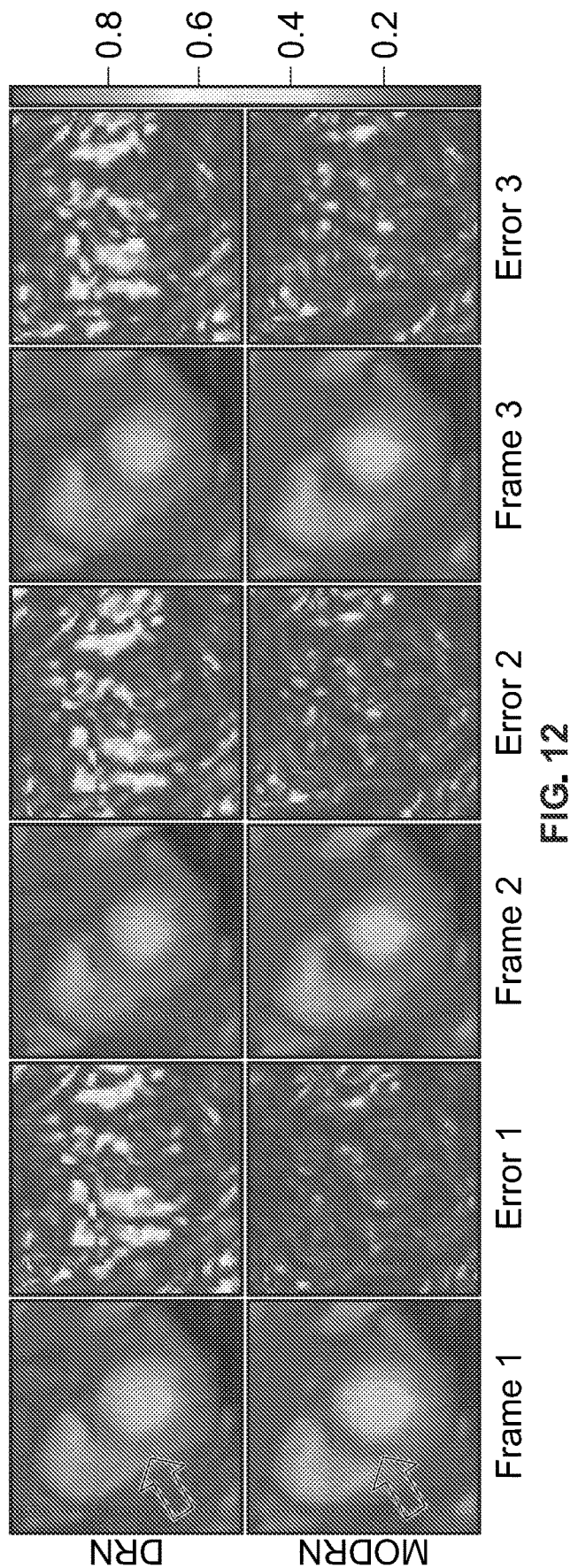

We visualize the reconstructed images and error with respect to ground truth of all methods in FIG. 11. It is obvious that all CS-based methods have streaking artifacts and larger reconstruction error while our MODRN model eliminates the most blurring artifacts and recovers more high-frequency details.

TABLE 5

| Method | Dice↑ | HD↓ |
| --- | --- | --- |
| Reference | 0.8130 | 1.9254 |
| Lucas-Kanade | 0.8125 | 1.9577 |

TABLE 5-continued

| Method | Dice↑ | HD↓ |
| --- | --- | --- |
| U-FlowNet-A | 0.8297 | 1.8755 |
| U-FlowNet-B | 0.8306 | 1.8584 |

The motion estimation results generated by the U-FlowNet were estimated from the ME component. Two baseline methods, Reference and Lucas-Kanade, are compared with our U-FlowNet-A (trained with only neighboring loss) and U-FowNet-B (trained with combined loss). Reference method directly calculates metrics using the segmentation of the target phase and the reference phase. Since it is impractical to obtain the ground truth of optical flow from cardiac MR, we compute the overlapped area of the myocardium between the targeting image and the warping image. In particular, we calculate the average Dice's score and Hausdorff Distance between $Z_1$ and other frames, $Z_T$ and other frames and also neighboring frames. The results of 3-fold cross-validation are reported in Table 5 above. We observe that U-FowNet-B method achieves the best performance, which indicates that compared with neighboring loss, our combined loss contributes more to accurate motion estimation with large movement between frames.

Second, we compare the quality of motion-guided refined image by MC component of MODRN with that of reconstructed image by DRN alone. The results of three consecutive frames are visualized in FIG. 12. We can observe clear improvements of MODRN that its reconstruction error is reduced around cardiac region and no noticeable artifact is generated.

Figure 13:
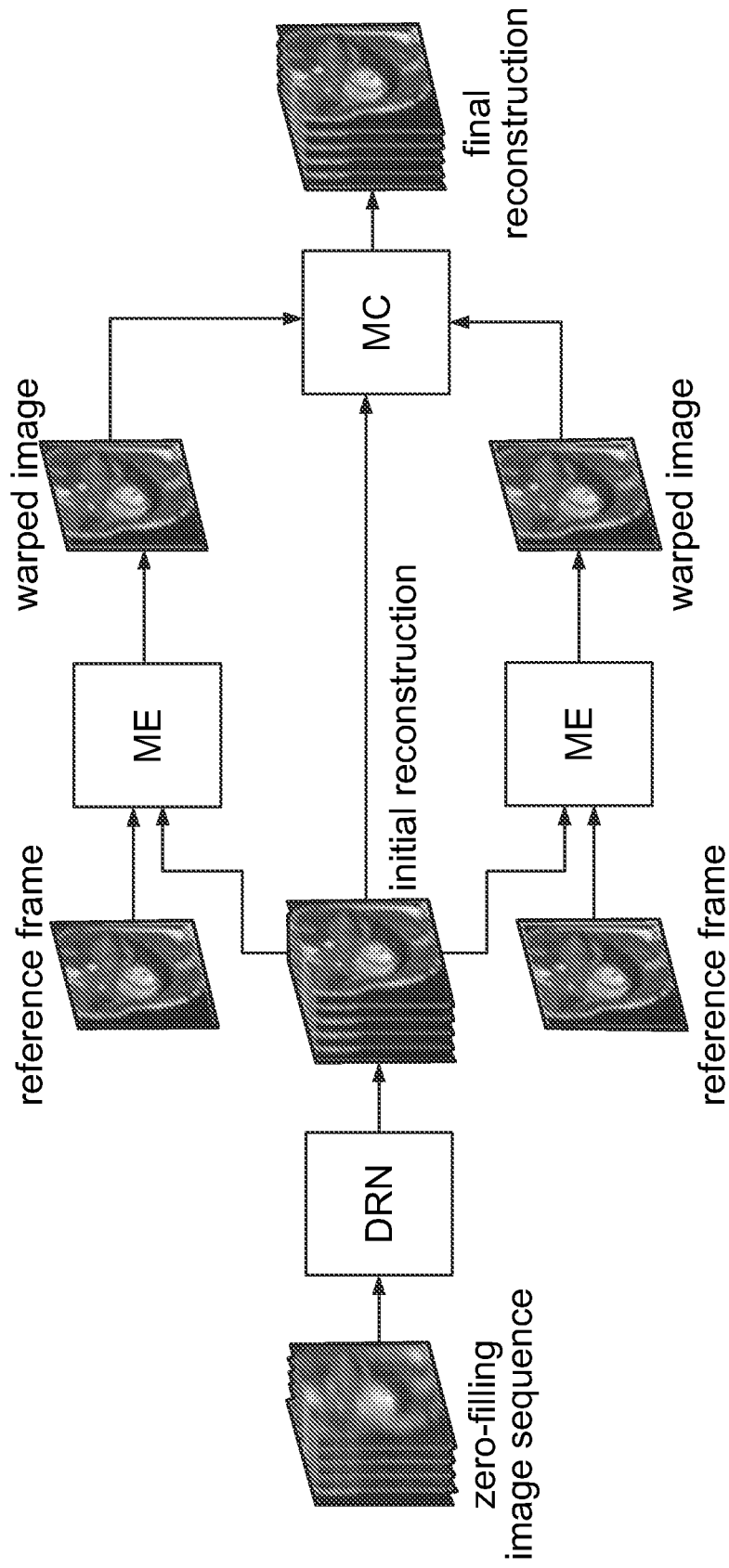
FIG. 13 is a diagram illustrating the motion-guided network of the present disclosure implemented as a single, differentiable network.

FIG. 13 is a diagram illustrating the motion-guided network discussed above in connection with process 16c, implemented as a single, differentiable network. As can be seen, the network includes the DRN discussed above as the first layer of the differentiable network, which receives as input a zero-filling image sequence (a Fourier transform of under-sampled k-space sequences). The DRN outputs an initial reconstruction series of images. Two ME components are provided in a second layer of the differentiable network, and each processes both the initial reconstruction series of images and a reference frame and outputs a warped image. The warped images are then processed by the MC component (which forms the third layer of the differentiable network) to output a final reconstruction. The differentiable network shown in FIG. 13 provides an end-to-end model that improves the performance of the MODRN network discussed above. Training in such an end-to-end manner is beneficial for allowing gradients from the MC component to be backpropagated to the ME components as well as to the DRN. Because of this, the ME components and the DRN are not only optimized for motion estimation and initial reconstruction, but also for generating final, motion-guided frames.

Having thus described the system and method in detail, it is to be understood that the foregoing description is not intended to limit the spirit or scope thereof. It will be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure. What is desired to be protected by Letters Patent is set forth in the following claims.

What is claimed is:

1. A method for joint reconstruction and segmentation of organs from magnetic resonance imaging (MRI) data, comprising the steps of:
   receiving MRI data at a computer system;
   processing the MRI data using a joint reconstruction and segmentation process to identify an organ from the MRI data;
   processing the MRI data using a channel-wise attention network to perform static reconstruction of the organ from the MRI data; and
   processing the MRI data using a motion-guided network to perform dynamic reconstruction of the organ from the MRI data.

2. The method of claim 1, wherein said processing steps are performed jointly by the computer system.

3. The method of claim 1, wherein the step of processing the MRI data using the joint reconstruction and segmentation process further comprises processing the MRI data using a first neural network to generate a reconstructed image from the MRI data.

4. The method of claim 3, wherein the step of processing the MRI data using the joint reconstruction and segmentation process further comprises processing the reconstructed image using a second neural network to identify contours of an organ in the reconstructed image.

5. The method of claim 1, wherein the step of processing the MRI data using the channel-wise attention network further comprises processing the MRI data using an undersampled mask and undersampled k-space data by the channel-wise attention network.

6. The method of claim 5, wherein the channel-wise attention network comprises a channel attention layer and a data consistency layer, the data consistency layer cascaded with the channel attention layer and processing outputs of the channel attention layer.

7. The method of claim 1, wherein the step of processing the MRI data using the motion-guided network comprises processing the MRI data using a recurrent process to dynamically reconstruct the organ in the presence of motion.

8. The method of claim 1, wherein the step of processing the MRI data using the motion-guided network comprises processing the MRI data using a differentiable network.

9. The method of claim 8, wherein the differentiable network includes a first layer comprising a dynamic reconstruction network, a second layer comprising a plurality of motion estimation components, and a third layer comprising a motion compensation component.

10. The method of claim 9, further comprising backpropagating gradients from the motion compensation component to the dynamic reconstruction network and the plurality of motion estimation components to improve training of the differentiable network.

11. A system for joint reconstruction and segmentation of organs from magnetic resonance imaging (MRI) data, comprising:
   a memory storing MRI data; and
   a processor in communication with the memory, the processor programmed to:
      process the MRI data using a joint reconstruction and segmentation process to identify an organ from the MRI data;
      process the MRI data using a channel-wise attention network to perform static reconstruction of the organ from the MRI data; and
      process the MRI data using a motion-guided network to perform dynamic reconstruction of the organ from the MRI data.

12. The system of claim 11, wherein processor processes the MRI data using a first neural network to generate a reconstructed image from the MRI data.

13. The system of claim 12, wherein the processor processes the reconstructed image using a second neural network to identify contours of an organ in the reconstructed image.

14. The system of claim 11, wherein the processor processes the MRI data using an undersampled mask and undersampled k-space data by the channel-wise attention network.

15. The system of claim 14, wherein the channel-wise attention network comprises a channel attention layer and a data consistency layer, the data consistency layer cascaded with the channel attention layer and processing outputs of the channel attention layer.

16. The system of claim 11, wherein the processor processes the MRI data using a recurrent process to dynamically reconstruct the organ in the presence of motion.

17. The system of claim 11, wherein the processor processes the MRI data using a differentiable network.

18. The system of claim 17, wherein the differentiable network includes a first layer comprising a dynamic reconstruction network, a second layer comprising a plurality of motion estimation components, and a third layer comprising a motion compensation component.

19. The system of claim 18, wherein the differentiable network backpropagates gradients from the motion compensation component to the dynamic reconstruction network and the plurality of motion estimation components to improve training of the differentiable network.

20. The system of claim 11, wherein the processor is in communication with or forms part of a magnetic resonance imaging (MRI) scanner.

21. A method for reconstruction of organs from magnetic resonance imaging (MRI) data, comprising the steps of:
receiving MRI data at a computer system;
processing the MRI data using a channel-wise attention network to perform static reconstruction of the organ from the MRI data; and
displaying the reconstructed organ.

22. The method of claim 21, wherein the step of processing the MRI data using the channel-wise attention network further comprises processing the MRI data using an undersampled mask and undersampled k-space data by the channel-wise attention network.

23. The method of claim 22, wherein the channel-wise attention network comprises a channel attention layer and a data consistency layer, the data consistency layer cascaded with the channel attention layer and processing outputs of the channel attention layer.

24. A method for reconstruction of organs from magnetic resonance imaging (MRI) data, comprising the steps of:
receiving MRI data at a computer system;
processing the MRI data using a motion-guided network to perform dynamic reconstruction of the organ from the MRI data; and
displaying the reconstructed organ,
wherein the step of processing the MRI data using the motion-guided network comprises processing the MRI data using a differentiable network.

25. The method of claim 24, wherein the step of processing the MRI data using the motion-guided network comprises processing the MRI data using a recurrent process to dynamically reconstruct the organ in the presence of motion.

26. The method of claim 24, wherein the differentiable network includes a first layer comprising a dynamic reconstruction network, a second layer comprising a plurality of motion estimation components, and a third layer comprising a motion compensation component.

27. The method of claim 24, further comprising backpropagating gradients from the motion compensation component to the dynamic reconstruction network and the plurality of motion estimation components to improve training of the differentiable network.

* * * * *

UNITED STATES PATENT AND TRADEMARK OFFICE
CERTIFICATE OF CORRECTION

PATENT NO. : 11,645,791 B2
APPLICATION NO. : 17/072632
DATED : May 9, 2023
INVENTOR(S) : Huang et al.

It is certified that error appears in the above-identified patent and that said Letters Patent is hereby corrected as shown below:

On the Title Page

Item (72), under Inventors, Qiaoying Huang's residential information delete "Edision, NJ" and replace with "Bellevue, WA"

Item (57), under the Abstract, Line 10, the word "can" should be deleted

Signed and Sealed this
Fifth Day of September, 2023

*Katherine Kelly Vidal*
Katherine Kelly Vidal
*Director of the United States Patent and Trademark Office*